(12) United States Patent
Richelson et al.

(10) Patent No.: US 6,472,209 B1
(45) Date of Patent: *Oct. 29, 2002

(54) USING POLYAMIDE NUCLEIC ACID OLIGOMERS TO ENGENDER A BIOLOGICAL RESPONSE

(75) Inventors: Elliott Richelson, Ponte Vedra Beach, FL (US); Beth Marie Tyler, Neptune Beach, FL (US); Daniel J. McCormick, Rochester, MN (US); Bernadette Marie Cusack, Jacksonville Beach, FL (US); Clark V. Hoshall, Ponte Vedra Beach, FL (US); Christopher Lee Douglas, Jacksonville, FL (US); Karen Jansen, Jacksonville, FL (US)

(73) Assignee: Mayo Foundation for Medical Education and Research, Rochester, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/953,269

(22) Filed: Oct. 17, 1997

(51) Int. Cl.$^7$ ............... C07H 21/04; C12N 15/00; A61K 48/00

(52) U.S. Cl. ............... 435/375; 435/6; 435/377; 514/44; 536/24.5; 536/24.1; 536/18.7

(58) Field of Search ............... 435/6, 375, 377; 514/44, 2; 536/24.5, 24.1, 18.7

(56) References Cited

U.S. PATENT DOCUMENTS

| | | | |
|---|---|---|---|
| 5,142,047 A | 8/1992 | Summerton et al. | 544/118 |
| 5,217,866 A | 6/1993 | Summerton et al. | 435/6 |
| 5,470,974 A | 11/1995 | Summerton et al. | 544/118 |
| 5,539,082 A | 7/1996 | Nielsen et al. | 530/300 |

(List continued on next page.)

FOREIGN PATENT DOCUMENTS

| | | |
|---|---|---|
| WO | WO 95/01370 | 1/1995 |
| WO | WO 95/04748 | 2/1995 |
| WO | WO 95/04749 | 2/1995 |
| WO | WO 96/35705 | 11/1996 |

(List continued on next page.)

OTHER PUBLICATIONS

Pooga et al., "Cell Penetrating PNA constructs Regulate Galanin Receptor Levels and Modify Pain Transmission in vivo" Nature Bioltechnology vol. 16: 857–861, Sep. 1998.*
Branch, A. "A Good Antisense Molecule is Hard to Find" TIBS vol. 23:45–50, Feb. 1998.*

(List continued on next page.)

Primary Examiner—Sean McGarry
(74) Attorney, Agent, or Firm—Fish & Richardson P.C., P.A.

(57) ABSTRACT

The invention involves methods and materials for extracellularly administering PNA oligomers to living cells. Specifically, the invention provides methods of treating living cells with PNA oligomers such that the oligomers cross biological barriers and engender a biological response in a sequence specific manner. This invention also provides methods of screening potential PNA oligomers for the ability to engender a sequence specific biological response. Further, this invention provides methods of identifying the function of polypeptides and of determining the relative turnover rate of functional polypeptides.

52 Claims, 9 Drawing Sheets

U.S. PATENT DOCUMENTS

| | | | |
|---|---|---|---|
| 5,773,571 A | 6/1998 | Nielsen et al. | 530/300 |
| 5,783,682 A | 7/1998 | Cook et al. | 536/24.3 |
| 5,786,461 A * | 7/1998 | Buchardt et al. | 536/18.7 |

FOREIGN PATENT DOCUMENTS

| | | |
|---|---|---|
| WO | WO 97/38013 | 10/1997 |
| WO | WO 97/41150 | 11/1997 |
| WO | WO 98/53801 | 12/1998 |
| WO | WO 99/05302 | 2/1999 |
| WO | WO 99/13719 | 3/1999 |
| WO | WO 99/13893 | 3/1999 |
| WO | WO 99/20643 | 4/1999 |

OTHER PUBLICATIONS

Norton et al. "Inhibition of Human Telomerase Activity by Peptide Nucleic Acids" Nature Biotechnology vol. 14:615–619, May 1996.*

Crooke, S., "Antisense '97: A Roundtable on the state of the industry," *Nature Biotechnology*, 15:519–524 (1997).

Gura, T., "Antisense Has Growing Pains," *Science*, 270:575–577 (1995).

Langel U. et al., "Cell penetrating PNA constructs," *J. Neurochem.* 69:B (1997).

Norton JC et al., "Inhibition of human telomerase activity by peptide nucleic acids," *Nature Biotechnology* 14:615–619 (1996).

Pardridge WM "Vector–mediated drug delivery of antisense therapeutics through the blood–brain barrier," *J. Neurochem.* 69:A (1997).

McMahon et al. "Altering behavioral responses and dopamine transporter protein with antisense peptide nucleic acids" (submitted for publication).

McMahon et al. "Extracranial injection of antisense peptide nucleic acids targeted to the mu receptor decreases response to morphine and receptor protein levels in rat brain" (submitted for publication).

McMahon et al. "Peptide Nucleic Acids Specifically Cause Antigene Effects in vivo" (submitted for publication).

Basu S. and Wickstrom E., "Synthesis and Characterization of a Peptide Nucleic Acid Conjugated to a D–Peptide Analog of Insulin–like Growth Factor 1 for Increased Cellular Uptake," *Bioconjugate Chem.* 8:481–488 (1997).

Bonham et al., "An Assessment of the Antisense Properties of RNase H–Competent and Steric–Blocking Oligomers," *Nucleic Acids Res.* 23:1197–1203 (1995).

Corey D.R., "Peptide Nucleic Acids: Expanding the Scope of Nucleic Acid Recognition," *Trends in Biotech.* 15:224–229 (1997).

Crooke S.T. et al., "Pharmacokinetic Properties of Several Novel Oligonucleotide Analogs in Mice," *J. Pharm. Exp. Ther.* 277:923–937 (1996).

Demidov V.V. et al., "Stability of Peptide Nucleic Acids in Human Serum and Cellular Extracts," *Biochem. Pharmacol.* 48:1310–1313 (1994).

Fraser G.L. et al., "In Vivo Modulation of Gene Expression by a Peptide Nucleic Acid Oligomer Antisense to the σ–Opioid Receptor," Abstracts—*Society of Neuroscience* 23:267.4 (1997).

Gambacorti–Passerini C. et al., "In Vitro Transcription and Translation Inhibition by Anti–Promyelocytic Leukemia (PML)/Retinoic Receptor α and Anti–PML Peptide Nucleic Acid," *Blood* 88:1411–1417 (1996).

Good L. and Nielsen P.E., "Progress in Developing PNA as a Gene–Targeted Drug," *Antisense Nucleic Acid Drug Dev.* 7:431–437 (1997).

Gray G.D. et al., "Transformed and Immortalized Cellular Uptake of Oligodeoxynucleoside Phosphorothioates, 3'–Alkylamino Oligodeoxynucleotides, 2'–O–methyl Oligoribonucleotides, Oligodeoxynucleoside Methylphosphonates, and Peptide Nucleic Acids," *Biochem. Pharmacol.* 53:1465–1476 (1997).

Hanvey J.C. et al., "Antisense and Antigene Properties of Peptide Nucleic Acids," *Science* 258:1481–1485 (1992).

Hyrup B. and Nielsen P.E., "Peptide Nucleic Acids (PNA): Synthesis, Properties and Potential Applications," *Bioorg. Med. Chem.* 4:5–23 (1996).

Knudsen H. and Nielsen P., "Application of Peptide Nucleic Acid in Cancer Therapy," *Anti–Cancer Drugs* 8:113–118 (1997).

Koppelhus U. et al., "Efficient in Vitro Inhibition of HIV–1 Gag Reverse Transcription by Peptide Nucleic Acid (PNA) at Minimal Ratios of PNA/RNA," *Nucleic Acids Res.* 25:2167–2173 (1997).

Mardirossian K. et al., "In Vivo Hybridization of Technetium–99m–Labeled Peptide Nucleic Acid (PNA)," *J. Nuc. Med.* 38:907–913 (1997).

Nielsen P.E. et al., "Peptide Nucleic Acid (PNA). A DNA Mimic With a Peptide Backbone," *Bioconjugate Chem.* 5:3–7 (1994).

Pardridge W.M. et al., "Vector–Mediated Delivery of a Polyamide ("Peptide") Nucleic Acid Analogue Through the Blood–Brain Barrier in Vivo," *Proc. Natl. Acad. Sci. USA* 92:5592–5596 (1995).

Peffer N.J. et al., "Strand–Invasion of Duplex DNA by Peptide Nucleic Acid Oligomers," *Proc. Natl. Acad. Sci. USA* 90:10648–10652 (1993).

Praseuth D. et al., "Peptide Nucleic Acids Directed to the Promoter of the α–Chain of the Interleukin–2 Receptor," *Biochim. Biophys. Acta.* 1309–226–238 (1996).

Rossi G. et al., "Blockade of Morphine Analgesia by an Antisense Oligodeoxynucleotide Against the Mu Receptor, " *Life Sciences* 54:PL375–PL379 (1994).

Scarfi S. et al., "Synthesis, Uptake, and Intracellular Metabolism of a Hydrophobic Tetrapeptide–Peptide Nucleic Acid (PNA)–Biotin Molecule," *Biochem. Biophys. Res. Commun.* 236:323–326 (1997).

Tanaka K. et al., "Structure and Functional Expression of the Cloned Rat Neurotensin Receptor," *Neuron* 4:847–854 (1990).

Taylor R.W. et al., "Selective Inhibition of Mutant Human Mitochondrial DNA Replication in Vitro by Peptide Nucleic Acids," *Nat. Genet.* 15(2):212–215 (1997).

Vita N. et al., "Cloning and Expression of a Complementary DNA Encoding a High Affinity Human Neurotensin Receptor," *FEBS Letters* 317:139–142 (1993).

Wittung P. et al., "Phospholipid Membrane Permeability of Peptide Nucleic Acid," *FEBS Letters* 365–27–29 (1995).

Yazaki T. et al., "Treatment of Glioblastoma U–87 by Systemic Administration of an Antisense Protein Kinase C–α Phosphorothioate Oligodeoxynucleotide," *Mol. Pharm.* 50:236–242 (1996).

* cited by examiner

SEQUENCE LISTING

<160> NUMBER OF SEQ ID NOS: 2

<210> SEQ ID NO 1
<211> LENGTH: 12
<212> TYPE: DNA
<213> ORGANISM: Rat

<400> SEQUENCE: 1
cattgctcaa ac                                                                12

<210> SEQ ID NO 2
<211> LENGTH: 14
<212> TYPE: DNA
<213> ORGANISM: Rat

<400> SEQUENCE: 2
cagcctcttc ctct                                                              14

USING POLYAMIDE NUCLEIC ACID OLIGOMERS TO ENGENDER A BIOLOGICAL RESPONSE

STATEMENT AS TO FEDERALLY SPONSORED RESEARCH

Funding for the work described herein was provided by the federal government, which may have certain rights in the invention.

BACKGROUND

1. Technical Field

The invention relates to administering polyamide nucleic acid oligomers to living cells such that the polyamide nucleic acid oligomers engender a sequence specific biological response.

2. Background Information

Polyamide nucleic acids (PNAs) are DNA analogs containing neutral amide backbone linkages. Unlike DNA oligomers, PNA oligomers can bind DNA by displacing one strand of the duplex to form a stable D-loop structure (Peffer et al., Proc. Natl. Acad. Sci. USA 90: 10648–10652 (1993) and Møllegaard et al., Proc. Natl. Acad. Sci. USA 91:3892–3895 (1994)). Interestingly, binding of PNA oligomers to DNA is independent of DNA strand polarity, allowing PNA oligomers to bind in both parallel and anti-parallel fashion (Egholm et al., Nature 365:566–568 (1993) and Peffer et al., Proc. Natl. Acad. Sci. USA 90:10648–10652 (1993)). In addition, PNA oligomers are less susceptible to enzymatic degradation (Demidov et al. Biochem. Pharmacol. 48:1310–1313 (1994)) and bind RNA with higher affinity than analogous DNA oligomers. Taken together, these properties suggest that PNA oligomers have great potential in both antigene and antisense approaches for regulating gene expression.

The success of an oligonucleotide analog as an antigene or antisense agent requires that the oligonucleotide be taken up by cells in reasonable quantities such that the oligonucleotide reaches its target at a sufficient concentration. PNA oligomers, however, have low phospholipid membrane permeability (Wittung et al., FEBS Letters 365:27–29 (1995)) and have been reported to be taken up by cells very poorly (Hanvey et al., Science 258:1481–1485 (1992); Nielsen et al., Bioconjugate Chem. 5:3–7 (1994); Bonham et al., Nucleic Acids Res. 23:1197–1203 (1995); Gray et al., Biochem. Pharmacol. 48:1465–1476 (1997)), which would appear to limit their potential uses in antigene and antisense approaches.

Recent strategies devised to improve cellular uptake of PNA oligomers involve conjugating other molecules to PNA sequences. Specifically, conjugating a small peptide sequence that binds the insulin-like growth factor 1 receptor (IGF1R) to a PNA oligomer increases cellular uptake of labeled PNA sequences by IGF1R-expressing cells, whereas conditions using unconjugated PNA sequences or cells lacking IGF1R show negligible cellular uptake (Basu S. and Wickstrom E., Bioconjugate Chem. 8:481–488 (1997)). These results suggest that conjugating receptor ligand molecules to PNA oligomers can increase cellular uptake; however, the ability of these receptor ligand-conjugated PNA oligomers to influence biological activity once inside the target cells remains unknown. Further, PNA oligomers will only gain entrance into cells expressing that particular targeted receptor. Thus, an appropriate ligand molecule would have to be designed and coupled to PNA oligomers for each cell type of interest. In addition, level of receptor expression can influence the permeability of ligand-conjugated PNA oligomers.

The use of PNA oligomers to manipulate brain protein expression, an approach that would greatly aid the understanding of brain function as well as neurological disease, has an additional problem. The endothelial wall of capillaries in both brain and spinal cord creates a barrier (blood-brain barrier; BBB) that excludes the uptake of molecules into these organs. Although specialized transport systems operate within the BBB to allow certain circulating molecules to cross, many pharmaceutical agents are not recognized and thus have poor BBB permeability. This appears true for PNA molecules since the transport of PNAs across the BBB is reported to be negligible (Pardridge et al., Proc. Natl. Acad. Sci. USA 92:5592–5596 (1995)). Therefore, PNA oligomers targeting brain proteins administered outside the central nervous system need to cross two barriers, the BBB and the plasma membrane of individual cells within brain, whereas PNA oligomers administered directly into brain need to cross one barrier, the plasma membrane of individual cells.

Various drug delivery strategies can circumvent the BBB permeability problem (Pardridge, Pharmacol. Toxicol. 71:3–10 (1992); Pardridge, Trends Biotechnol. 12:239–245 (1994)). For example, PNA molecules can undergo transport through the BBB when the amino terminus is biotinylated and linked to a streptavidin conjugated monoclonal antibody specific for transferrin receptor (OX26-SA; Pardridge et al., Proc. Natl. Acad. Sci. USA 92:5592–5596 (1995)). The OX26-SA antibody delivers linked molecules to brain presumably by receptor-mediated endocytosis, given the high transferrin receptor concentrations located on the BBB. These studies suggest that antibody-conjugation strategies provide a mechanism for PNA oligomers to cross the BBB. No data, however, exist as to whether the biotinylated PNA linked to OX26-SA actually enters cells or not. In addition, the utility of PNA delivery methods that rely on conjugating other molecules to PNA oligomers remains unclear since these other molecules may influence the desired functionality of particular PNAs. Therefore, strategies that enable PNA oligomers to cross biological barriers with minimal modifications of or additions to the PNA oligomer would be desirable with the ultimate goal, of course, being to influence biological activity in a sequence specific manner.

SUMMARY

The present invention relates to PNA oligomers that influence biological activity in a sequence specific manner. Specifically, this invention relates to the discovery that PNA oligomers administered extracellularly cross biological barriers and elicit a sequence specific biological response in living cells. This discovery is in direct opposition to the current understanding of the physical properties of PNA oligomers and has far-reaching implications for both gene therapy and research purposes. Further, extracellularly administering PNA oligomers to living cells circumvents the need to micro-inject PNA oligomers directly into cells as well as the need to permeabilize cells. In addition, this invention provides for the treatment of cells in vivo such that a behavioral response is observed in an organism. Thus, this invention describes methods and materials that allow any polypeptide to be manipulated and studied in living cells. For example, the expression of a specific polypeptide can be knocked-out in adult organisms for the duration of PNA oligomer treatment. In addition to greatly aiding the advancement of basic scientific research, this ability to manipulate polypeptide expression and thus function in a sequence specific manner is clearly beneficial to gene therapy approaches involving the treatment of cancer, aging, behavioral diseases, infections, and auto-immune diseases.

One aspect of the invention provides methods of treating living cells by extracellularly administering PNA oligomers under conditions such that the PNA oligomers engender a biological response in a sequence specific manner. The PNA oligomers can be carrier-free and can be in vivo administered to an animal. The PNA oligomers are capable of crossing biological barriers such as the plasma membrane of cells and the blood-brain barrier of a living organism. The PNA oligomers typically have sequence specificity for a nucleic acid sequence that encodes a polypeptide or regulates the expression of a polypeptide. The polypeptides can be expressed intracranially or extracranially in a living organism. Intracranially expressed polypeptides can include those polypeptides that participate in cell signaling. Cell signaling polypeptides include polypeptides that participate in opioid signaling. Opioid signaling polypeptides include opioid receptors, for example morphine and neurotensin receptors. Extracranially expressed polypeptides include polypeptides expressed outside the brain and cranium, for example in the gastrointestinal tract. Specific PNA oligomers can include oligomers having sequences such as set out in SEQ ID NO:s 1 and 2. The biological response engendered by the extracellular administration of PNA oligomers can be a modification, for example a reduction, of polypeptide expression. Biological responses also can be characterized by a physiological change in an animal.

Another aspect of the invention provides a method of screening PNA oligomers for the ability to engender a sequence specific biological response by extracellularly administering PNA oligomers to living cells. The PNA oligomers can be carrier-free and can be in vivo administered to an animal. The PNA oligomers are capable of crossing biological barriers such as the plasma membrane of cells and the blood-brain barrier of a living organism. The PNA oligomers typically have sequence specificity for a nucleic acid sequence that encodes a polypeptide or regulates the expression of a polypeptide. The polypeptides can be expressed intracranially or extracranially in a living organism. Intracranially expressed polypeptides can include those polypeptides that participate in cell signaling. Cell signaling polypeptides include polypeptides that participate in opioid signaling. Opioid signaling polypeptides include opioid receptors, for example morphine and neurotensin receptors. Extracranially expressed polypeptides include polypeptides expressed outside the brain and cranium, for example in the gastrointestinal tract. The biological response engendered by the extracellular administration of PNA oligomers can be a modification, for example a reduction, of polypeptide expression. Biological responses also can be characterized by a physiological change in an animal.

Another aspect of the invention relates to a method of identifying polypeptide function by extracellularly administering PNA oligomers to living cells such that the PNA oligomers alter the expression of the polypeptide in a sequence specific manner and examining those cells for an activity that is influenced by the specific PNA oligomer. The PNA oligomers can be carrier-free and can be in vivo administered to an animal, such as a murine mammal. The PNA oligomers are capable of crossing biological barriers such as the plasma membrane of cells and the blood-brain barrier of a living organism. The PNA oligomers typically have sequence specificity for a nucleic acid sequence that encodes a polypeptide or regulates the expression of a polypeptide. The polypeptides can be expressed intracranially or extracranially in a living organism. Intracranially expressed polypeptides can include those polypeptides that participate in cell signaling. Cell signaling polypeptides include polypeptides that participate in opioid signaling. Opioid signaling polypeptides include opioid receptors, for example morphine and neurotensin receptors. Extracranially expressed polypeptides include polypeptides expressed outside the brain and cranium, for example in the gastrointestinal tract. Specific PNA oligomers can include oligomers having sequences such as set out in SEQ ID NO:s 1 and 2. The biological response engendered by the extracellular administration of PNA oligomers can be a modification, for example a reduction, of polypeptide expression. Biological responses also can be characterized by a physiological change in an animal.

Another aspect of the invention involves a method of measuring the relative turnover rate of functional polypeptides having a defined activity by extracellularly administering PNA oligomers to living cells such that the PNA oligomers influence the defined activity, and determining the time after PNA oligomer administration that the defined activity is maximally influenced. In addition, the time from when the defined activity is influenced maximally to when the activity returns to normal can be determined.

Another aspect of the invention is an article of manufacture that combines packaging material and PNA oligomers. The packaging material includes a label or package insert indicating that the PNA oligomers can be extracellularly administered to living cells for the purpose of engendering a biological response in a sequence specific manner.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
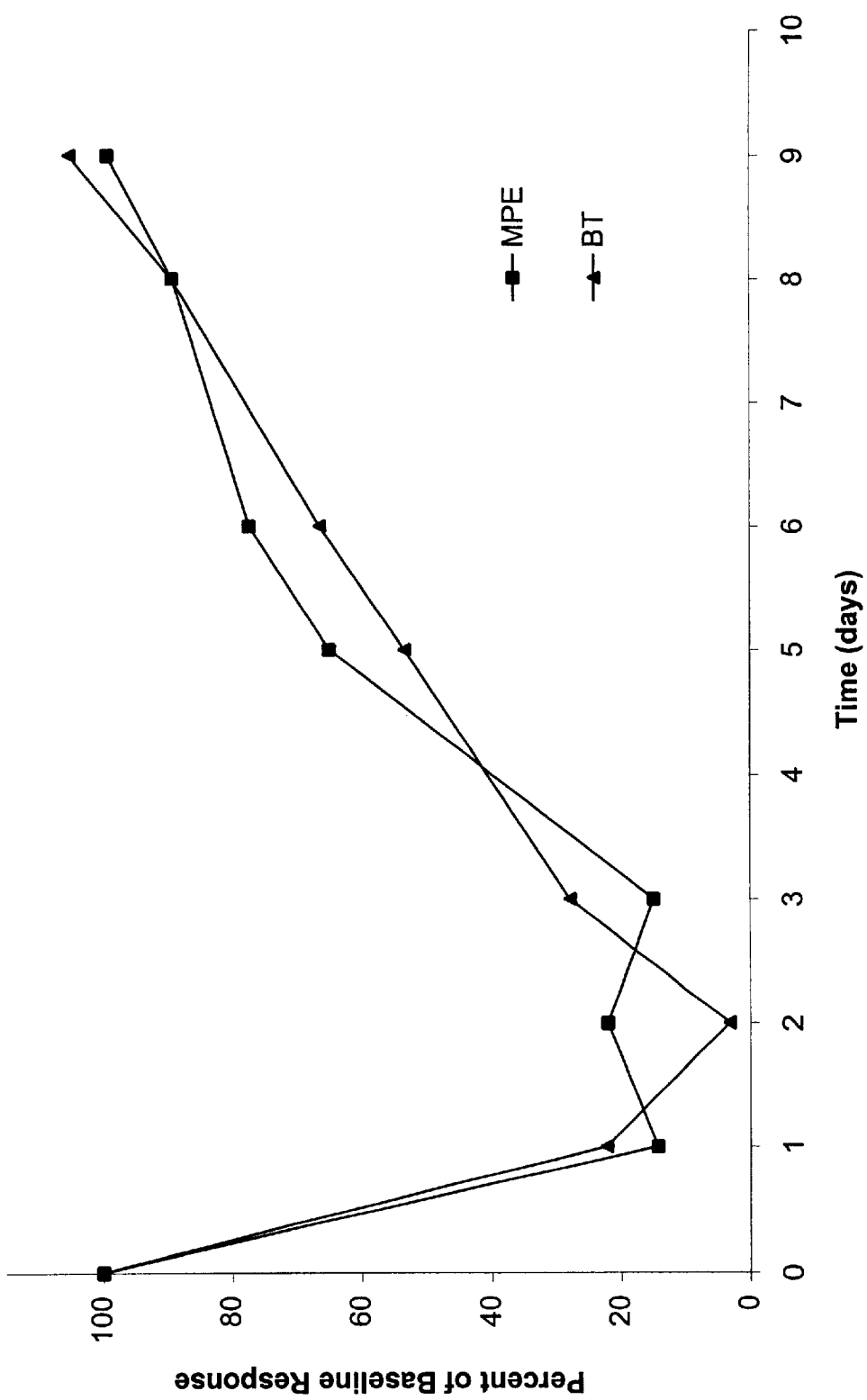
FIG. 1 is a graph plotting the maximal possible effect and body temperature as a percent of baseline response for rats treated intracranially on days –4, –2, and 0 with NTR1-PNA oligomers and challenged with NT.

The invention involves methods and materials for extracellularly administering PNA oligomers to living cells. Specifically, the invention provides methods of treating living cells with PNA oligomers such that the oligomers cross biological barriers and engender a biological response in a sequence specific manner. This invention also provides methods of screening potential PNA oligomers for the ability to engender a sequence specific biological response. Further, this invention provides methods of identifying the function of polypeptides and of determining the relative turnover rate of functional polypeptides.

Extracellularly Administering PNA Oligomers to Living Cells

PNA oligomers can be administered to living cells extracellularly such that they cross a biological barrier and engender a sequence specific biological response. That a PNA oligomer crosses a biological barrier can be inferred from the ability of the PNA oligomer to engender a sequence specific biological response requiring interactions with specific nucleic acid sequences contained within a living cell. For example, if a PNA oligomer having sequence specificity for the nucleic acid encoding protein X is administered extracellularly and engenders a sequence specific biological response by altering the expression of protein X, then it can be inferred that that particular PNA oligomer also crossed a biological barrier, the plasma membrane. In other words, the nature of sequence specific biological responses engendered by PNA oligomers implies that PNA oligomers crossed a biological barrier to interact with specific nucleic acid sequences within living cells. Thus, a sequence specific biological response is any response of a living cell that is attributed to the actual sequence of a PNA oligomer, such as the alteration of protein X expression as stated above. In addition to analyzing polypeptide expression, sequence specific biological responses can be determined by analyzing any biological activity including, without limitation, cellular activities such as signaling, adherence, movement, proliferation, differentiation, and apoptosis as well as physiological activities such as development, growth, reproduction, immunity, pain, anti-nociception, perception, depression, and memory.

PNA oligomers used to engender a sequence specific biological response in a living cell can be obtained from PerSeptive Biosystems (Framingham, Ma., USA) or from authorized suppliers. Alternatively, PNA oligomers can be synthesized manually from PNA monomers obtained from PerSeptive Biosystems as described elsewhere (Norton J. C., Bioorg. Med. Chem. 3:437–445 (1995) and Cory D. R., Trends in Biotech. 15:224–229 (1997)). PNA oligomers can be any length providing they contain at least two PNA monomers. Thus, PNA oligomers can range in size from dinucleotides to entire genes or more. PNA oligomers also can have any sequence providing the PNA oligomer crosses a biological barrier, such as the BBB of an organism or the plasma membrane of a cell, and engenders a sequence specific biological response. For example, a PNA oligomer can have sequence specificity for any nucleic acid sequence that encodes a polypeptide or regulates the expression of a polypeptide. With the current advances in recombinant nucleic acid and nucleic acid sequencing technology, countless nucleic acid sequences are not only known but also readily available from sequence databases such as Genebank®. In addition, PNA oligomers can be either modified or unmodified with the condition that they cross a biological barrier and engender a sequence specific biological response. Possible types of modification can include but are not limited to modifications with acridine, protein, backbone chemistries, DNA, peptide, bis-PNA, biotin, and fluorescein. Unmodified PNA oligomers can include any oligomer made essentially from PNA monomers, but without further modifications designed to enhance the crossing of plasma membranes or the BBB. Such unmodified PNA oligomers are designated herein as "carrier-free." It is to be understood, however, that "carrier-free" PNA oligomers can be modified in other ways, for example to enhance detectability (e.g., with various labels).

The mode of administering PNA oligomers to living cells can be any mode wherein the administration is extracellular and the administered PNA oligomers engender a sequence specific biological response. For example, PNA oligomers can be applied directly to tissue culture medium when treating cells in vitro or can be administered to an organism when treating cells in vivo. When treating cells in vivo, PNA oligomers can be administered by various routes. Various pharmaceutically acceptable carriers can be used for in vivo administration to animals, including for example physiological saline, artificial cerebral-spinal fluid, or other known carriers appropriate to specific routes of administration.

For the purpose of this invention, two general routes of administration are provided: intracranial and extracranial. Examples of intracranial routes of administration include but are not limited to intracisternal, intraventricular, and intradural. Examples of extracranial routes of administration include but are not limited to oral, intravenous, intramuscular, intraperitoneal, subcutaneous, intradermal, topical, or the like. The route of administration, whether intracranial or extracranial, can depend on a variety of factors, such as treatment environment and therapeutic goals. In addition, PNA oligomers may be administered on a continuous or an intermittent basis. Further, an extracellular administration of PNA oligomers can contain PNA oligomers having a single sequence specificity or can contain different PNA oligomers having a plurality of sequence specificities.

The dosages of PNA oligomers will depend on many factors including the mode of administration and the living cells being treated whether within a living organism or within culture. Typically, the concentration of PNA oligomers contained within a single dose will be an amount that effectively engenders a sequence specific biological response without inducing significant toxicity.

Screening Potential PNA Oligomers

Potential PNA oligomers can be screened for the ability to engender a desired biological response in a sequence specific manner. The desired sequence specific biological response can be any alteration of a particular activity or can be a specific level of alteration of a particular activity. For example, one desired sequence specific biological response could be any reduction in polypeptide expression, whereas another could be the complete knock-out of polypeptide expression. To screen potential PNA oligomers, single PNA oligomers or pools of different PNA oligomers are extracellularly administered to living cells as described above. After administration, the living cells are monitored for the desired sequence specific biological response. Particular pools of PNA oligomers that engender the desired sequence specific biological response can be divided and re-screened sequentially until a single PNA oligomer sequence is identified, if necessary.

Identifying Polypeptide Function

The function of any polypeptide expressed in a living cell can be identified by the following method. PNA oligomers having sequence specificity for the nucleic acid sequence that encodes a polypeptide or regulates the expression of a polypeptide can be administered extracellularly to living cells such that the expression of that particular polypeptide is altered in a sequence specific manner. After administration, the cells can be examined to determine an activity specifically influenced by the altered polypeptide expression caused by the administered PNA oligomers. Living cells can be treated either in vivo or in vitro and examined either in vivo or in vitro. For example, PNA oligomers can be administered to an organism and, after administration, cells taken from the organism for examination. In addition, PNA oligomers can be administered to an organism and the organism itself examined after administration. Thus, the examination of living cells can include, without limitation, examination of an organism. In addition to examining the living cells themselves after administration, any component of the living cells can be examined. For example, PNA oligomers can be administered to an organism and then cells can be extracted and manipulated so that a particular component of the cell is examined.

Measuring Relative Turn-over Rate

The relative turn-over rate of a functional polypeptide having a defined activity can be measured by the following method. PNA oligomers having sequence specificity for a nucleic acid sequence that encodes a particular polypeptide having a defined activity or that regulates the expression of the polypeptide can be administered extracellularly to living cells such that the defined activity attributed to the polypeptide is influenced in a sequence specific manner. The turn-over rate for the polypeptide can be determined by measuring the time, after administration, needed for the activity attributed to the polypeptide to be maximally influenced. In addition, the turn-over rate can be further defined by measuring the time needed for the maximally influenced activity to return to a normal level following removal of the PNA oligomers from the cellular environment. A normal level is the level of activity measured before any administration of PNA oligomers. From these data the relative turn-over rate of the polypeptide can be determined by comparison to turn-over rates of other polypeptides derived in a similar manner. These comparisons can be made between polypeptides with either similar or different biological activities.

The invention will be further described in the following examples, which do not limit the scope of the invention described in the claims.

EXAMPLES

Example 1

Extracellular Administration of PNA Oligomers Having Sequence Specificity for the Neurotensin Receptor-1

1. Synthesis of PNA Oligomers

The PNA oligomers were synthesized with Fmoc-N-(2-aminoethyl) glycyl PNA monomers on an Expidite 8909 Nucleic Acid Synthesizer according to the chemistry and protocols developed by the manufacturer (PerSeptive Biosystems, Inc., Framingham, Ma.). The exocyclic amines of the bases adenine, guanine, thymine, and cytosine of each Fmoc-PNA monomer were protected with the blocking group benzhydryloxycarbonyl (Bhoc). Synthesis of the PNA oligomers (2×2 μmol) was on polyamide linker (PAL)-Polyethylene Glycol-olystyrene resin (PerSeptive Biosystems, Inc.) which produces a carboxamide group ($CONH_2$) at the COOH terminus (3') end. After synthesis, the PNA was de-protected and removed from the resin by treatment with a mixture of 80% trifluoroacetic acid (TFA) containing 20% m-Cresol for 90 minutes at 22° C. The PNA oligomer was then precipitated in diethyl ether and purified by reverse phase high performance liquid chromatography on a Vydac $C_{18}$ column at 60° C. with a buffer of 0.1% aqueous TFA and a linear gradient of 0.5% TFA containing 80% acetonitrile/20% water. A major peak (@$A_{300}$ nm) was collected, lyophilized, and verified for its correct mass weight by electro-spray ionazation mass spectrometry on a Sciex API 165B mass spectrometer (Perkin-Elmer, Foster City, Calif.).

2. Neurotensin Receptor PNA Oligomers

Neurotensin (NT) is a tridecapeptide that produces a potent, naloxone-insensitive anti-nociceptive response as well as hypothermia when injected into the periaqueductal gray (PAG) region of the rat brainstem. Currently, two subtypes of NT receptors have been identified (NTR1 and NTR2), however, their exact involvement in NT-mediated anti-nociception and hypothermia remains unclear. In an attempt to characterize NT receptors and possibly identify additional subtypes, a PNA oligomer (NTR1-PNA) having sequence specificity for NTR1 was synthesized as described above. Specifically, this NTR1-PNA was a 12-mer having an antisense sequence beginning at +103 bp from the start site of the coding region of the recombinant rat NTR1. This region was selected because it is an area thought to have high secondary structure in the mRNA. This may not be important for binding of antisense PNA oligomers, which have higher affinity for complementary nucleic acids (both RNA and DNA) than does DNA. The sequence of NTR1-PNA is 5'-CATTGCTCAAAC-3' (SEQ ID NO: 1).

3. Injecting NTR1-PNA Oligomers Intracranially

Under an Institutional Animal Care and Use Committee approved protocol and under sterile conditions male Sprague-Dawley rats (180–200 g) were stereotaxically implanted with stainless steel guide cannulae (26 gauge) into the PAG under sodium pentobarbital anesthesia (50 mg/kg, i.p.) as described in detail elsewhere (Jensen T. S. and Yaksh T. L., Brain Res. 372: 301–312 (1986) and Al-Rodhan N. R. F., Brain Res. 557:227–235 (1991)). The coordinates used for PAG cannulations are −5.6 mm posterior from bregma, 1.0 mm lateral from bregma, and 5.5 mm down from the dura. The guide cannula was pre-measured to be 5.5 mm (Plastics One, Roanoke, Va.) and the internal cannula was ordered to fit below the pedestal with a 2.0 mm projection. The guide cannula was then fixed to the skull using a stainless steel screw (⅛ inch) and cranioplastic cement. A stainless steel stilette was then placed in each guide to keep it patent and free of debris. Immediately after surgery, the animals were allowed to recover before returning them to an individual housing cage. All injections began 5–7 days after surgery. If any problem, such as an infection, was observed with an animal after cannulation, then the animal was euthanized immediately by decapitation.

NTR1-PNA oligomers were injected, using a Hamilton digital syringe, into the PAG through the internal cannula, which extended 2 mm below the guide tip. The internal cannula was connected with a length of polyethylene tubing (PE-20) filled with saline solution. A small air bubble was introduced into the tubing to separate the saline from a solution containing 1.3 nmol of NTR1-PNA oligomers in artificial cerebral-spinal fluid (ACSF). The volume of the solution containing the NTR1-PNA oligomers was about 1.0 µl. The bubble was used to confirm the movement of this solution through the polyethylene tubing.

NTR1-PNA oligomers were injected into the PAG of each rat three times, on days −4, −2, and 0. Controls included rats receiving no injections, rats receiving injections of ACSF only, and rats receiving PNA oligomers having sequence specificity for an unrelated polypeptide, the mu-1 morphine receptor (MU1R). The sequence of MU1R-PNA is 5'-CAGCCTCTTCCTCT-3' (SEQ ID NO: 2).

4. Analysis of Neurotensin-mediated Biological Responses

The injection of NT in the PAG of rats produces a potent anti-nociceptive response as well as hypothermia. These responses are mediated by specific NT receptors and are not inhibited by naloxone. A very sensitive and reliable hot plate test was used to measure the anti-nociceptive effects of NT (Al-Rodhan N. R. F., Brain Res. 557:227–235 (1991)).

NTR1-PNA, MU1R-PNA, and ACSF treated as well as untreated rats were analyzed using the hot plate test for NT. One day after the last treatment, each rat was analyzed as follows. Fifteen minutes prior to testing, a pre-drug latency measurement was made by placing the rat on a hot plate maintained at a temperature of $52\pm0.15°$ C. and recording the time elapsed before the rat licked either of its hindpaws. In addition, the temperature of the rat was taken using a thermister probe inserted 3 cm in the rectum to determine the pre-drug body temperature (BT). After making these measurement, an appropriate dose of NT (18 nmol) at a volume of about 0.5 µl was administered into the PAG as described above. Thirty minutes after administering NT, the rat was again placed on a hot plate maintained at a temperature of $52\pm0.15°$ C. and the latency between the time the rat was placed on the surface and the time it licked either of its hindpaws was measured. Failure to respond in 30 seconds resulted in the removal of the rat to prevent tissue damage and the assignment of that latency. Hot plate tests were scored as the percent of maximum possible effect (% MPE) and calculated using the following equation: %MPE=[(post-drug latency—pre-drug latency)/(cut-off- pre-drug latency)]×100; where the cut-off is 30 seconds. Untreated control rats are NT responsive and had a significant change within the 30 second time test averaging 75% +9% MPE. This average for untreated control rats was used to set the baseline MPE value to 100. Immediately after the 30 second hot plate test, BT was taken to measure NT-induced hypothermia using a thermister probe inserted 3 cm in the rectum. Again, untreated control rats are NT responsive and had a significant temperature change averaging $-1.81\pm0.26°$ C., which was used to set the baseline BT value to 100. All test situations were compared to these baseline values derived from NT responsive untreated controls.

On the last day of testing, 0.5 µl of methylene blue was injected into the PAG of each rat. The rat then was decapitated and the brain removed to verify the placement of the cannula. Each brain was placed in 10% formalin/sucrose for 3 days and frozen sections (30 µm thick) were taken coronally along a plane parallel to the injection cannula. The sections were stained with Crystal violet, photographed, and compared to stereotaxic plates. The results presented were derived from rats having the correct cannula location.

Data were tested for significance by the Student's t-test with $p<0.05$ being considered significant.

FIG. 1 depicts the MPE and BT responses to NT challenge as a percent of baseline response for rats treated with NTR1-PNA oligomers as described above. Each rat received three injections of NTR1-PNA oligomers on days −4, −2, and 0. The 100 percent value on day zero was derived from untreated control rats, whereas the NTR1-PNA treated rats were first analyzed one day after the last injection on day 0. Both the NT-mediated anti-nociceptive (MPE) and hypothermia (BT) responses were significantly reduced at day one after NTR1-PNA treatment and remained significantly reduced until day five for anti-nociception and day six for hypothermia. Responsiveness to NT challenge gradually returned to normal from days five to nine. In addition, both behavioral responses were correlated having nearly identical levels of reduction, recovery, and rates of recovery.

Figure 2:
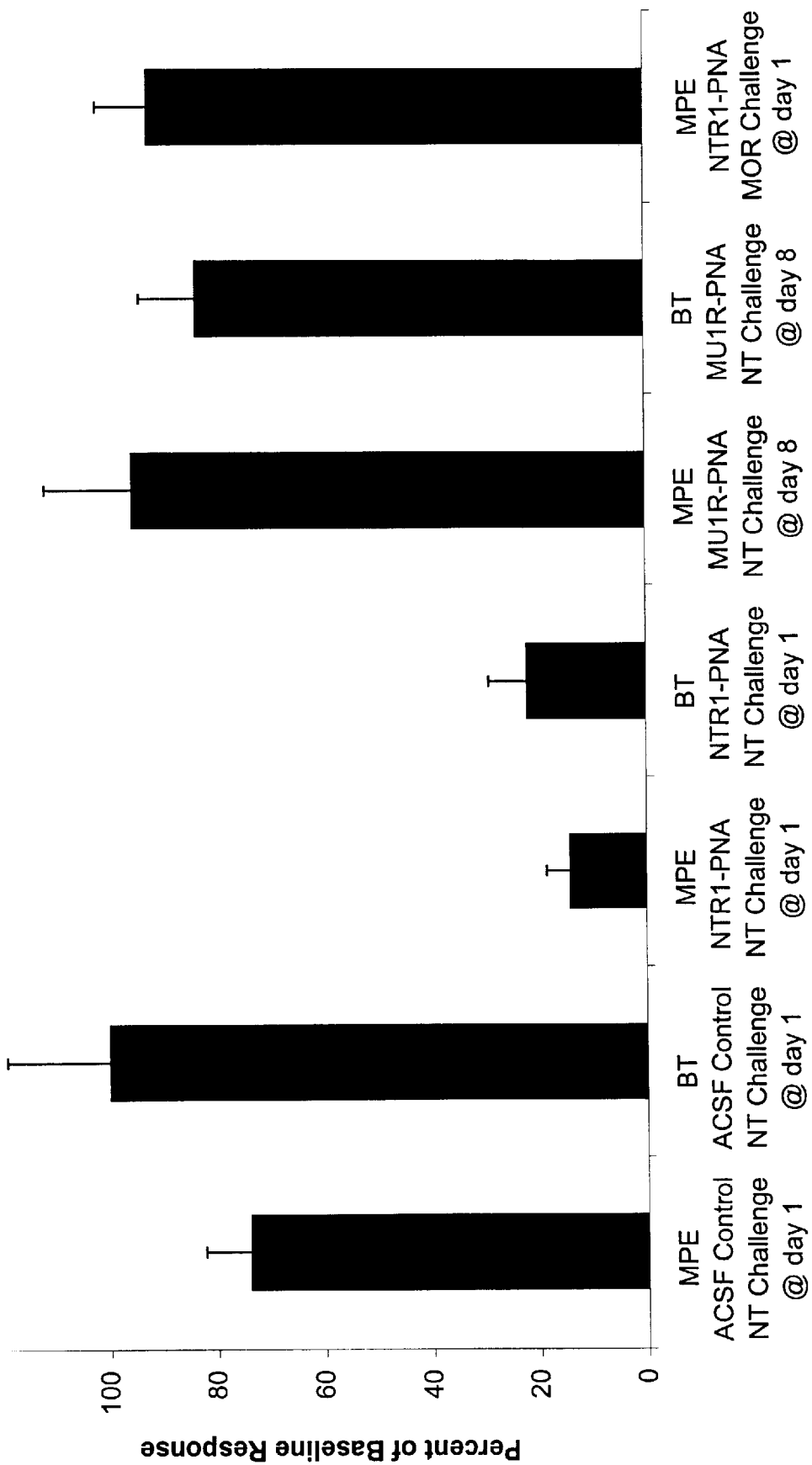
FIG. 2 is a bar graph depicting the maximal possible effect and body temperature as a percent of baseline response for rats receiving the indicated PNA oligomer treatments intracranially on days –4, –2, and 0 and challenged with either NT or MOR on the days indicated.

FIG. 2 is a bar graph that depicts the sequence specific effects of NTR1-PNA oligomer treatment. The MPE and BT for each type of treatment was determined as a percent of baseline response by NT challenge. The MPE and BT values derived from rats injected with ACSF only and challenged with NT were equivalent to baseline responses. These animals were completely responsive to NT challenge, exhibiting little or no reaction to pain as well as a decreased body temperature. Rats injected with NTR1-PNA oligomers, however, exhibited little response to NT challenge. In fact, the MPE and BT responses to NT challenge for NTR1-PNA treated rats were 10 to 30 percent of the baseline responses. As a control to indicate the sequence specific nature of the PNA oligomer influence on these biological responses, the NT responsiveness of rats injected with MU1R-PNA oligomers was analyzed. The MPE and BT values derived from rats injected with MU1R-PNA oligomers and challenged with NT were indistinguishable from the baseline responses, indicating that the NTR1-PNA oligomers engender a biological response in a sequence specific manner. As another control, rats injected with the NTR1-PNA oligomers were analyzed for morphine (MOR) responsiveness using a tail flick assay (see Example 2 below). The MPE for rats treated with NTR1-PNA oligomers and challenged with MOR was similar to baseline response values, again indicating the specificity of the NTR1-PNA oligomers.

5. Identifying the Function of Neurotensin-1 Receptors

As stated above, two subtypes of NT receptors have been identified and additional, currently unidentified, NT receptor subtypes may exist. Further, the exact involvement of NTR1 and NTR2 in NT-mediated anti-nociception and hypothermia remains unclear. For example, NTR1 could primarily mediate anti-nociception and NTR2 could primarily mediate hypothermia or vice versa. The results described above, however, indicate that NTR1 participates significantly in both NT-mediated anti-nociception and hypothermia responses (FIGS. 1 and 2). In fact, both biological responses are correlated having nearly identical levels of reduction, recovery, and rates of recovery (FIG. 1). This identification of NTR1 function is based on the fact that the specific sequence of NTR1-PNA is not present in NTR2 and the assumption that the sequence of NTR1-PNA is unique to only NTR1 and not any other unidentified NT receptor subtypes.

6. Analysis of Neurotensin Receptors

In addition to determining the influence of NTR1-PNA oligomers on anti-nociception and hypothermia, the effects of these oligomers on NT binding sites were determined using the following NT receptor binding assay.

Binding assays were done with homogenates from rat PAG and hypothalamus tissue as described elsewhere (Kanba et al., J. Neurochem. 46:946–952 (1986) and Al-Rodhan N. R. F., Brain Res. 557:227–235 (1991)). Tissue concentrations were 1 mg wet weight per tube in a total volume of 100 μl with a final buffer concentration of 0.05 M Tris-HCl (pH 7.4) containing the following compounds to inhibit degradation of peptides: 0.02% (w/v) bovine serum albumin, 2.8 mg/ml bacitracin, 1.0 mM EDTA, 0.5 mM o-phenanthroline, 10 μg/ml pepstatin, 10 μg/ml leupeptin, 10 μg/ml aprotinin, 5 mM benzamidine, 2 mM phenylmethylsulfonylfluoride, and 50 μM bestatin. For each experiment, 80 μl of a thawed membranal suspension was incubated for 25 minutes at 20° C. in a solution containing 0.2 nM [$^{125}$I]neurotensin with a final volume of 100 μl. After incubation, the mixture was rapidly filtered to separate bound from unbound radioligand. Each filter was then dried for 2 minutes, placed on a solid scintillation sheet (Wallac Oy, Turku Finland; cat. no. 1205–441), and measured for radioactivity in a beta-plate scintillation counter (Wallac Oy; model # 1205 beta plate). Non-specific binding of [$^{125}$I] neurotensin, defined as the binding in the presence of 1 μM neurotensin (~20% of total binding), was subtracted from the total binding to calculate the specific binding.

The LIGAND program was used to analyze all binding data (Munson P. J. and Rodbard D., Analyt. Biochem. 107:220–239 (1980)). Specifically, this program was used to calculate equilibrium dissociation constants and maximal number of binding sites.

Table I contains the results from several [$^{125}$I]neurotensin binding assays. The analysis of PAG tissue in experiment 1 was as follows. Four rats were cannulated and treated on days −4, −2, and 0 with either ACSF only or NTR1-PNA as described above. One day after the final treatment, the PAG region of the rat brain was removed, homogenized, and used in the binding assays. Rats treated with ACSF only were used to derive control values for the percent control disintegrations per minute (dpm) and percent control receptors (fmol/mg wet weight). Thus, the values for ACSF only treated rats were set to 100 percent. One day after the final treatment, the PAG region from NTR1-PNA oligomer treated rats expressed 60–70 percent fewer [$^{125}$I]neurotensin binding sites than ACSF only treated rats.

In experiment 2, five rats were untreated and used as controls, two recovered rats were treated with ACSF only, and four rats were treated with NTR1-PNA oligomers. The two rats treated with ACSF only are designated as recovered since both rats previously received a single dose of PNA oligomers intraperitoneally (one received NTR1-PNA oligomers and the other MU1R-PNA oligomers). These rats, however, were not used until five days after the intraperitoneal (i.p.) PNA oligomer treatment. Thus, at the time the binding analysis was performed, these rats were completely normal as determined by the behavioral NT-mediated responses and the MOR-mediated response described above. Again, one day after the final treatment, the PAG region from NTR1-PNA oligomer treated rats expressed fewer [$^{125}$I]neurotensin binding sites than both the recovered ACSF only treated rats and untreated control rats. In this experiment, the reduction in binding sites was about 20–30 percent of those expressed by the untreated rats. Further, the previously treated recovered rats that received ACSF only expressed significantly more NT binding sites than the untreated control rats, possibly indicating the involvement of a compensatory mechanism operating at the level of receptor densities.

NT binding sites from the hypothalamus region of the rat brain were also analyzed. In this experiment, the hypothalamus region of rat brain was removed from the same rats used in experiment 2 to analyze the PAG region (five untreated control rats, two recovered ACSF only treated rats, and four NTR1-PNA oligomer treated rats). The untreated rats were used to derive control values. One day after the final treatment, the hypothalamus region from NTR1-PNA oligomer treated rats expressed 40–50 percent fewer [$^{125}$I] neurotensin binding sites than untreated control rats. In addition to indicating that extracellularly administered PNA oligomers influence the expression of specific polypeptide, these results demonstrate that PNA oligomers injected into the PAG diffuse through brain tissue to the hypothalamus since the NTR1-PNA oligomers were injected into the PAG and not the hypothalamus.

TABLE I

[$^{125}$I]neurotensin binding sites from rats 6 days after chronic treatment with NTR1-PNA oligomers

| PAG Tissue | n | % Control dpm's | % Control receptors |
|---|---|---|---|
| Experiment 1: | | | |
| ACSF Only | 2 | 100 | 100 |
| NTR1-PNA | 2 | 411 | 32 |
| Experiment 2: | | | |
| Untreated Control | 5 | 100 | 100 |
| Recovered* | 2 | 160 | 137 |
| NTR1-PNA | 4 | 81 | 67 |
| Hypothalamus Tissue | | | |
| Untreated Control | 5 | 100 | 100 |
| Recovered* | 2 | 136 | 101 |
| NTR1-PNA | 4 | 55 | 51 |

*Two previously treated rats, one treated intraperitoneally with NTR1-PNA and another with MU1R-PNA, were characterized behaviorally as fully recovered and normal.

7. Injecting NTR1-PNA Oligomers Extracranially

Figure 3:
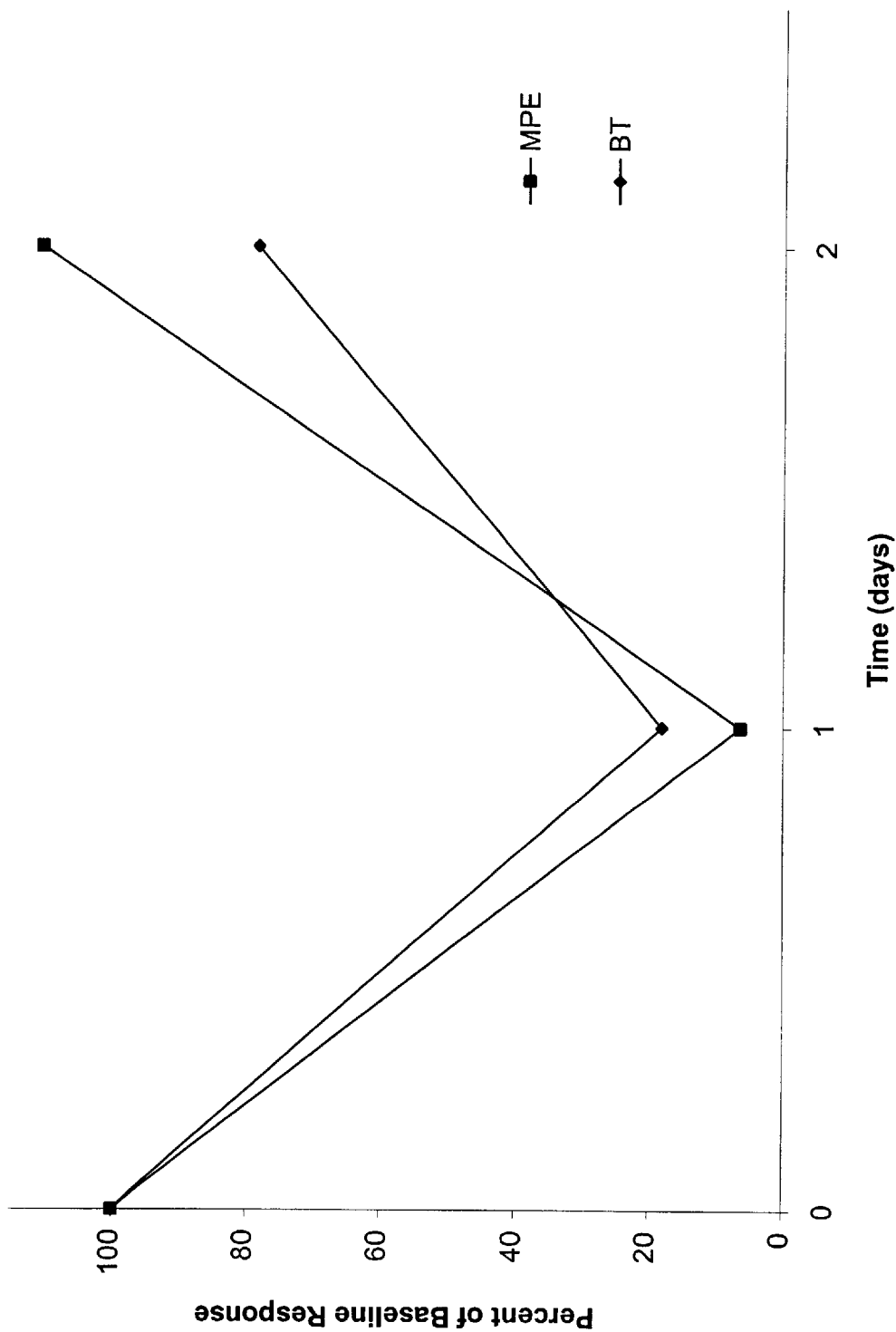
FIG. 3 is a graph plotting the maximal possible effect and body temperature as a percent of baseline response for rats treated extracranially on day 0 with NTR1-PNA oligomers and challenged with NT.
Figure 4:
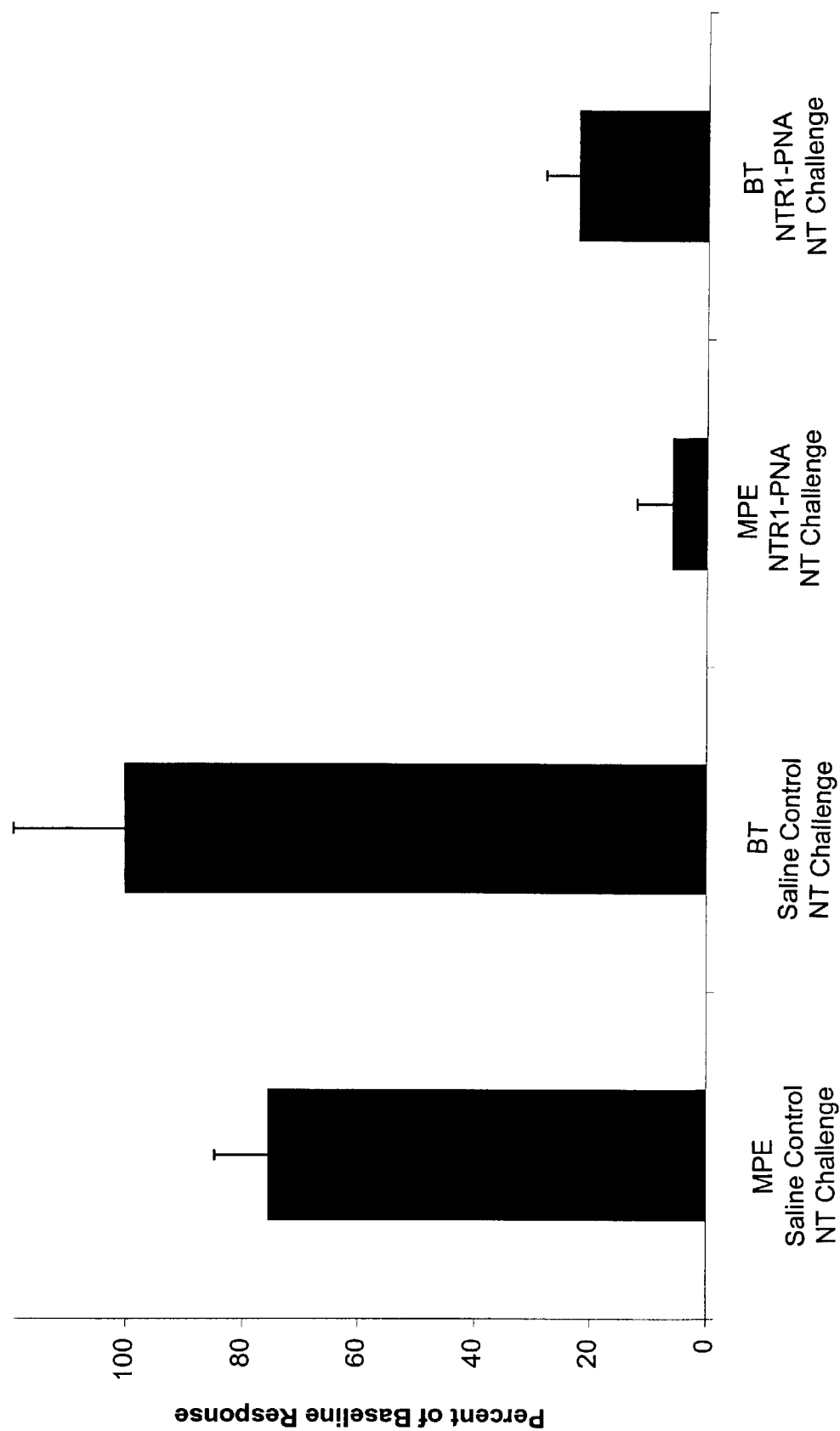
FIG. 4 is a bar graph depicting the maximal possible effect and body temperature as a percent of baseline response for rats receiving either a NTR1-PNA oligomer or saline treatment extracranially on day 0 and challenged with NT on day 1.

A solution containing 3 mg/kg of body weight of NTR1-PNA oligomers in saline was injected directly into the peritoneal cavity of male Sprague-Dawley rats (200–250 g). Each rat received a single injection on day zero and the volume injected was about 200 μl. Controls included rats receiving no injections and injections of saline only. Each day after the injection, the rats were analyzed for NT-mediated anti-nociceptive and hypothermia responses. FIG. 3 depicts the MPE and BT as a percent of baseline response for NT challenge. Baseline responses were measured from control animals not receiving injections and set to 100. Rats, however, were surgically cannulated to enable NT administration. One day after treatment with NTR1-PNA oligomers, rats were unable to respond to NT challenge. This inability to respond to NT challenge was identical to the inability observed from the PAG injections and is attributed to a reduction in NT receptors. In addition, FIG. 4 depicts the MPE and BT as a percent of baseline responses for NTR1-PNA treated, NT challenged rats as well as saline only treated, NT challenged rats at day 1. Only rats treated with NTR1-PNA oligomers exhibited a lack of NT responsiveness as determined by NT-mediated anti-nociception and hypothermia responses. Thus, NTR1-PNA oligomers administered extracranially were able to cross the BBB and the plasma membrane of cells to specifically influence the expression and thus the function of NT receptors in brain.

8. Analysis of Neurotensin Receptors Outside Brain

In addition to determining the influence of extracranially administered NTR1-PNA oligomers on anti-nociception and hypothermia, the effects of these oligomers on NT binding sites outside the central nervous system were determined.

Binding assays were performed using procedures similar to those described elsewhere (Kitabgi P. et al., Peptides 5:917–923 (1984) and Ahmad S. et al., Biochim et Biophys Acta 896:224–238 (1987)).

Table II contains the results from an [$^{125}$I]neurotensin binding assay using small intestine (jejunum and ileum) membranal preparations from NTR1-PNA treated and untreated rats. The small intestine tissue was harvested from the rats 1 day after receiving a single i.p. injection of NTR1-PNA oligomers as described above. Untreated rats were used to derive control values for the percent control dpm and percent control receptors (fmol/mg). Thus, the values for untreated rats were set to 100 percent. One day after treatment, the small intestine tissue from NTR1-PNA treated rats expressed 98 percent fewer [$^{125}$I]neurotensin binding sites than untreated rats, indicating that NTR1-PNA oligomers administered extracranially engender a biological response in both brain and the periphery (small intestine cells). These results indicate that the extracranial administration of PNA oligomers can engender a sequence specific biological response systemically.

TABLE II

[$^{125}$I]neurotensin binding sites from rats 1 day after i.p. treatment with NTR1-PNA oligomers

| Small Intestine | n | % Control dpm's | % Control receptors |
| --- | --- | --- | --- |
| Untreated Control | 2 | 100 | 100 |
| NTR1-PNA | 1 | 41 | 2 |

Example 2

Extracellular Administration of PNA Olihomers Having Sequence Specificity for the Mu-1 Receptor

1. Morphine Receptor PNA Oligomer Synthesis and Intracranial Administration Morphine (MOR) produces a potent, naloxone-sensitive anti-nociceptive response in animals. This anti-nociceptive response is mediated by MOR receptors. PNA oligomers having sequence specificity for the mu-1 receptor (MU1R-PNA) were designed and synthesized as described above. The MU1R-PNA oligomers are 14-mers having an antisense sequence corresponding to approximately −50 bp from the start site of the coding region of the recombinant mu-1 receptor. Thus, the MU1R-PNA does not have sequence specificity for the coding region of the mu-1 receptor gene, but does have sequence specificity for an upstream sequence presumed to be involved in regulating the expression of mu-1 receptors. In addition, this region is not predicted to have a high degree of secondary structure at the mRNA level. The sequence of MU1R-PNA is 5'-CAGCCTCTTCCTCT-3' (SEQ ID NO: 2). MU1R-PNA oligomers were injected into the PAG region of cannulated rats as described above.

2. Analysis of Morphine-mediated Biological Responses

The injection of MOR into rats produces a potent anti-nociceptive response. This response is mediated by specific MOR receptors and is inhibited by naloxone. A very sensitive and reliable tail flick test was devised and used to measure the anti-nociceptive effects of MOR (D'Amour F. E. and Smith D. L, J. Pharm. Exp. Therap. 72:74–79 (1941)). MU1R-PNA, NTR1-PNA, and ACSF treated as well as untreated rats were analyzed using the MOR-specific tail flick test. One day after the last treatment, each rat was analyzed as follows. Thirty minutes prior to testing, a pre-drug latency measurement was made by placing the tail of the restrained rat in oil maintained at a temperature of 60° C. and recording the time elapsed before the rat flicked its tail. After making this measurement, an appropriate dose of MOR (5 mg/kg of body weight) at a volume of about 200 µl was injected i.p. Thirty minutes after administering MOR, the restrained rat's tail was again placed in the oil maintained at 60° C. and the latency between the time the tail was placed in the oil and the time the rat flicked its tail was measured. Failure to respond in 12 seconds resulted in the removal of the rat's tail to prevent tissue damage and the assignment of that latency. Tail flick tests were scored as the percent of MPE and calculated using the following equation: %MPE=[(post-drug latency—pre-drug latency)/(cut-off-pre-drug latency)]×100; where the cut-off is 12 seconds. Untreated control rats are MOR responsive and had a significant change within the 12 second time test averaging 86%±5.2% MPE. This average for untreated control rats was used to set the baseline MPE value to 100. All test situations were compared to this baseline response value derived from MOR responsive untreated controls. To test the significance, data were analyzed using the Student's t-test with $p<0.05$ being considered significant.

Figure 5:
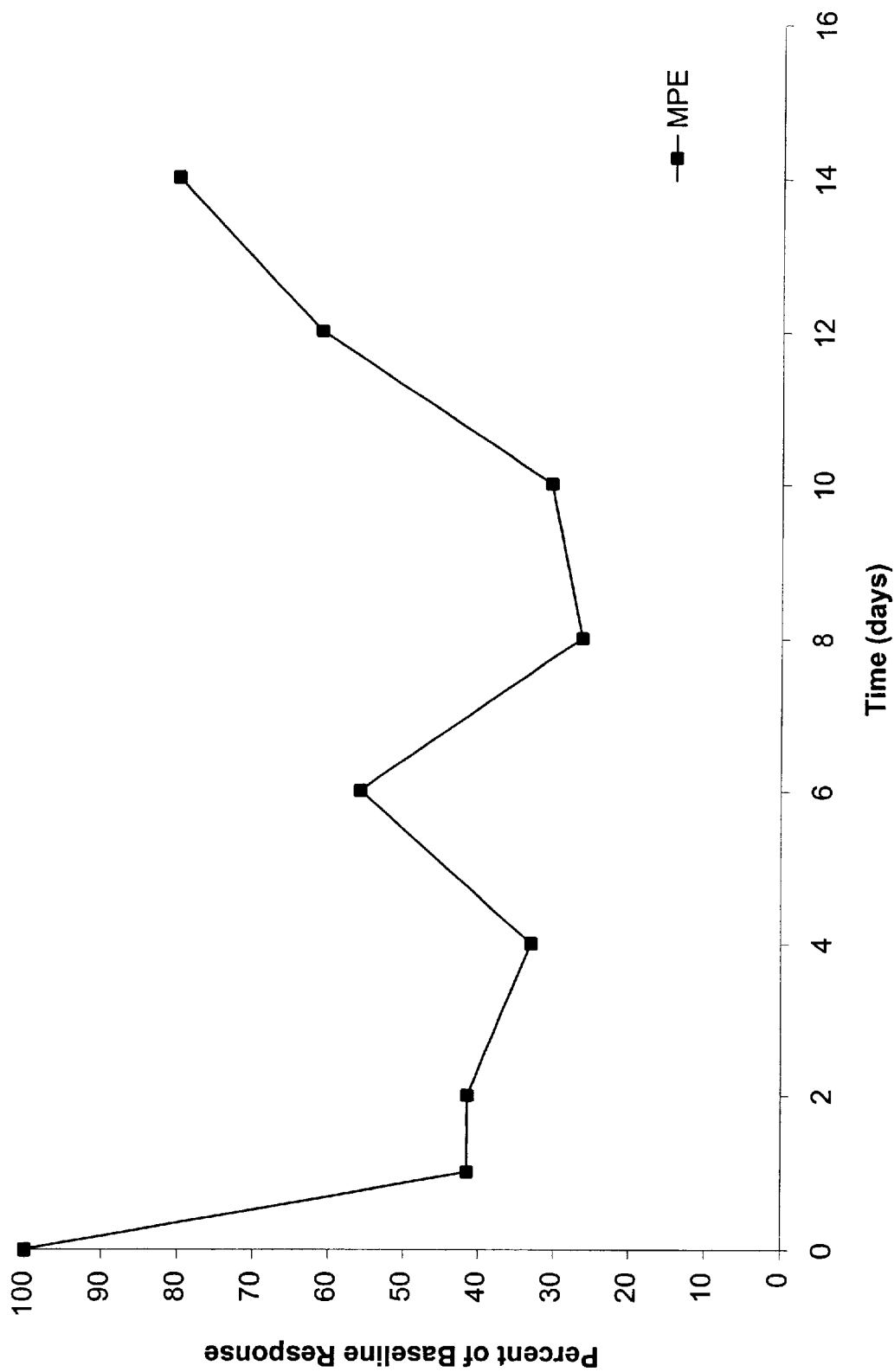
FIG. 5 is a graph plotting the maximal possible effect as a percent of baseline response for rats treated intracranially on days −4, −2, and 0 with MU1R-PNA oligomers and challenged with MOR.

FIG. 5 depicts the MPE response to MOR challenge as a percent of baseline response for rats treated with MU1R-PNA oligomers as described above. Each rat received three injections of MU1R-PNA oligomers on days −4, −2, and 0. The 100 percent value on day zero was derived from untreated control rats, whereas the MU1R-PNA treated rats were first analyzed one day after the last injection on day 0. The MOR-mediated anti-nociceptive response was significantly reduced at day one after MU1R-PNA treatment and remained significantly reduced until day twelve. Responsiveness to MOR challenge gradually returned to normal after day twelve.

Figure 6:
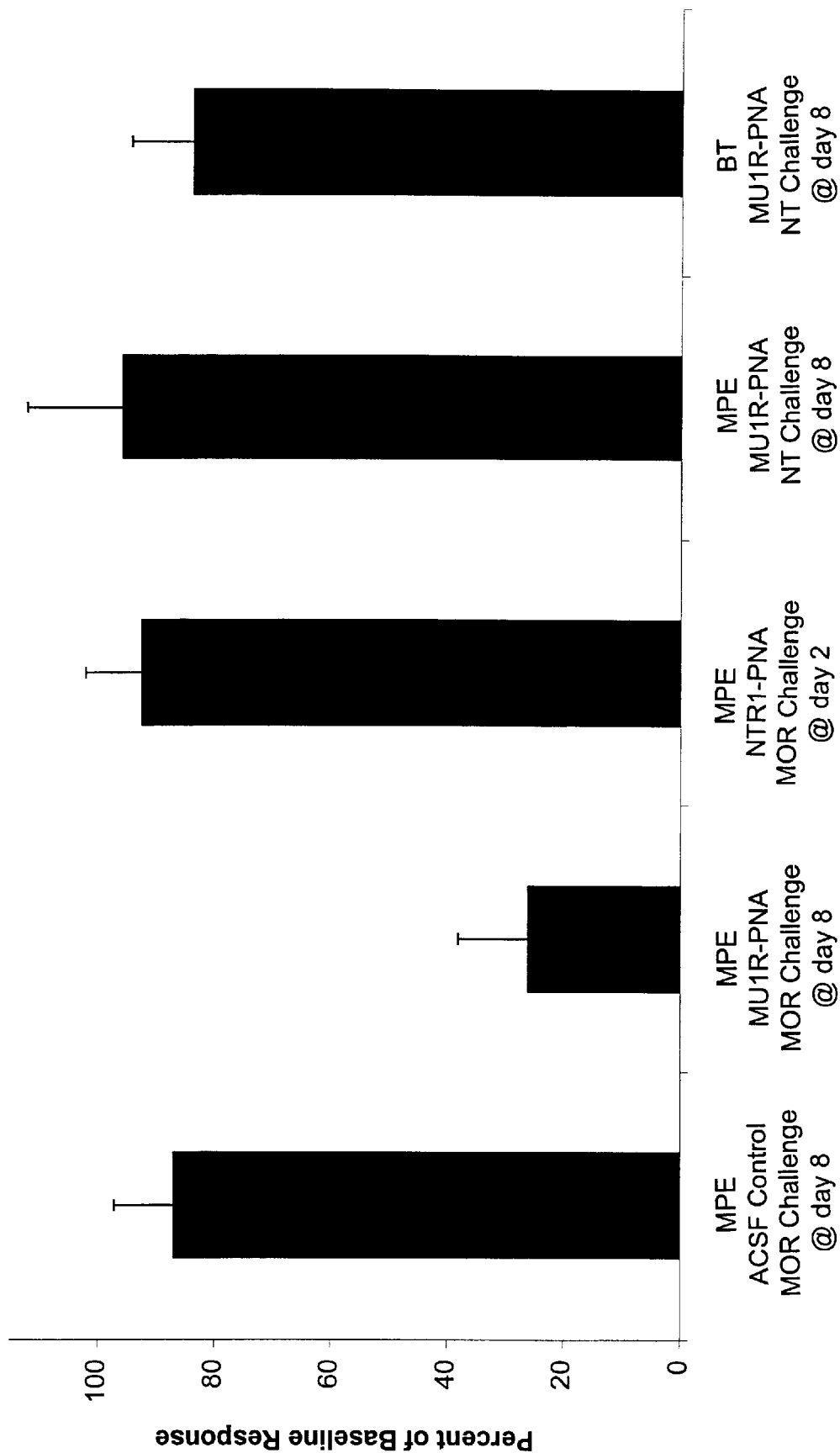
FIG. 6 is a bar graph depicting the maximal possible effect and body temperature as a percent of baseline response for rats receiving the indicated PNA oligomer treatments intracranially on days −4, −2, and 0 and challenged with either NT or MOR on the days indicated.

FIG. 6 is a bar graph that depicts the sequence specific effect of MU1R-PNA oligomer treatment. The MPE response to MOR challenge as a percent of baseline response was determined for each type of treatment. The MPE values derived from rats injected with ACSF only and challenged with MOR were equivalent to baseline responses. These animals were completely responsive to MOR challenge, exhibiting no reaction to pain. Rats injected with MU1R-PNA oligomers, however, exhibited little response to MOR challenge. In fact, the tail flick response to MOR challenge for MU1R-PNA treated rats was 20 to 40 percent of baseline response. As a control to indicate the sequence specific nature of the PNA oligomer influence on this biological response, the MOR responsiveness of rats injected with NTR1-PNA oligomers was analyzed. The MPE values derived from rats injected with NTR1-PNA oligomers and challenged with MOR were indistinguishable from baseline responses, indicating that the MU1R-PNA oligomers engender a biological response in a sequence specific manner. As another control, rats injected with the MU1R-PNA oligomers were analyzed for NT responsiveness using the hot plate test described above as well as measuring hypothermia. The MPE and BT responses for rats treated with MU1R-PNA oligomers and challenged with NT were similar to baseline response values, again indicating the specificity of MU1R-PNA oligomers.

3. Injecting MU1R-PNA Oligomers Extracranially

Figure 7:
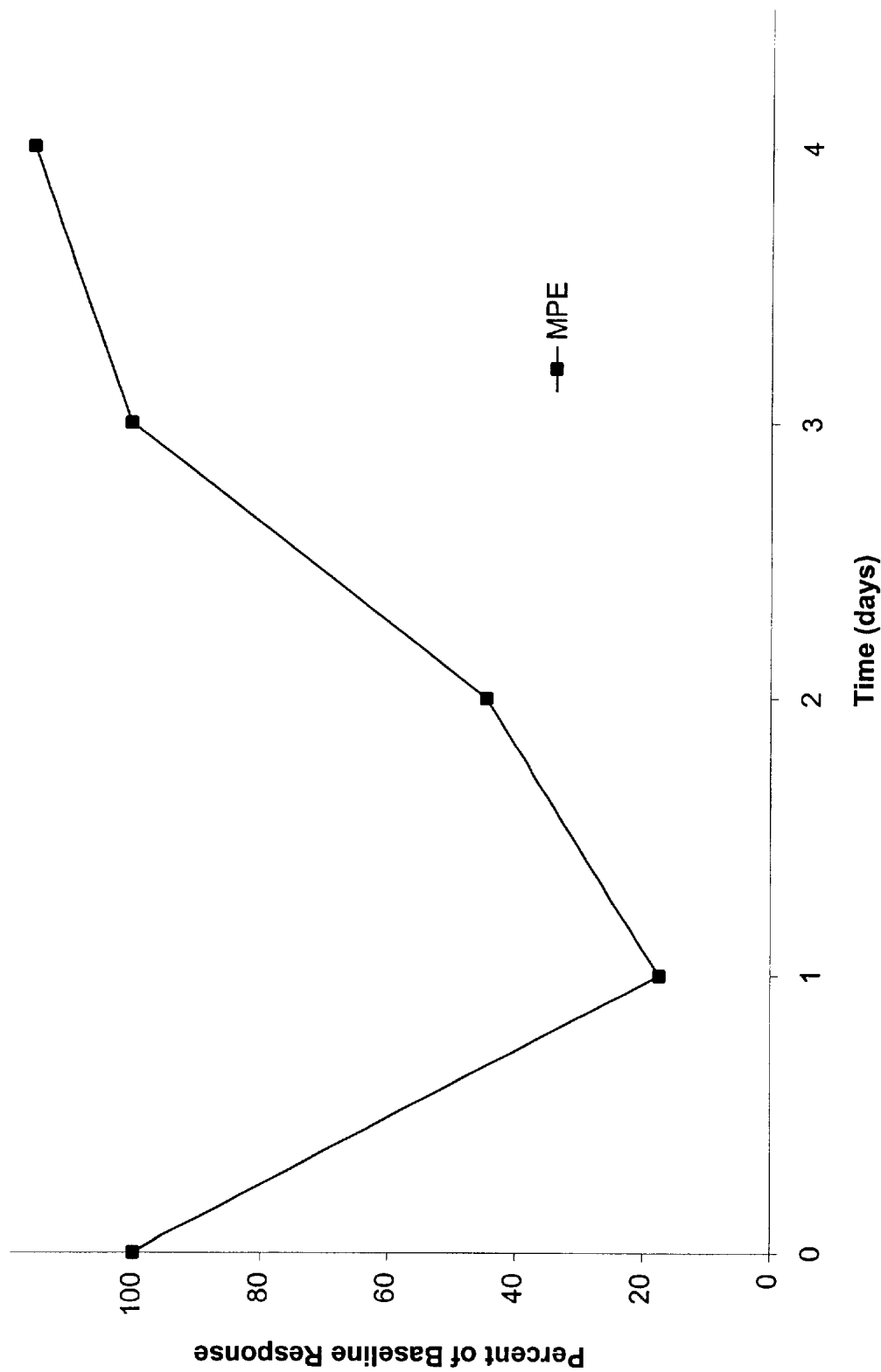
FIG. 7 is a graph plotting the maximal possible effect as a percent of baseline response for rats treated extracranially on day 0 with MU1R-PNA oligomers and challenged with MOR.
Figure 8:
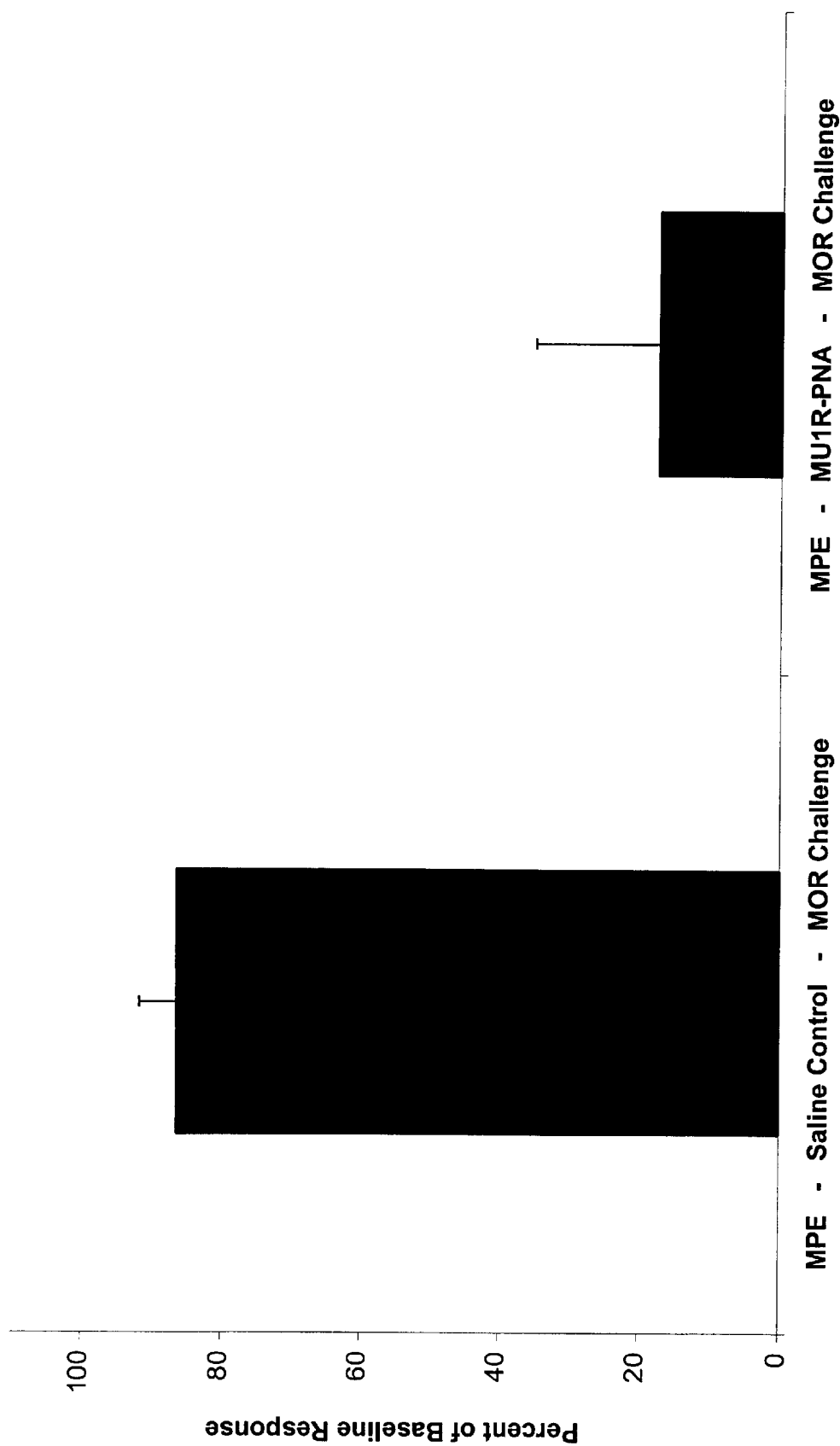
FIG. 8 is a bar graph depicting the maximal possible effect as a percent of baseline response for rats receiving either a MU1R-PNA oligomer or saline treatment extracranially on day 0 and challenged with MOR on the day 1.

A solution containing 3 mg/kg of body weight of MU1R-PNA oligomers in saline was injected directly into the peritoneal cavity of male Sprague-Dawley rats (200–250 g). Each rat received a single injection on day zero and the volume injected was about 200 µl. Controls included rats receiving no injections and injections of saline only. Each day after the injection, the rats were analyzed for MOR-mediated anti-nociception. FIG. 7 depicts the MPE response to MOR challenge as a percent of baseline response. Baseline responses were measured from control animals not receiving injections and set to 100. One day after treatment with MU1R-PNA oligomers, rats were unable to respond to MOR challenge. This inability to respond to MOR challenge was identical to the inability observed from the PAG injections and is attributed to a reduction in mu-1 receptors. In addition, FIG. 8 depicts the MPE response to MOR challenge for MU1R-PNA treated rats as well as rats treated with only saline at day 1. Only rats treated with MU1R-PNA oligomers exhibited a lack of MOR responsiveness as determined by the tail flick anti-nociceptive response to MOR. Thus, MU1R-PNA oligomers administered extracranially were able to cross the BBB and the plasma membrane of cells to specifically influence the expression and thus the function of mu-1 receptors in a sequence specific manner in bram.

4. Determining the Relative Turn-over Rate for Neurotensin-1 and Mu-1 Receptors

Figure 9:
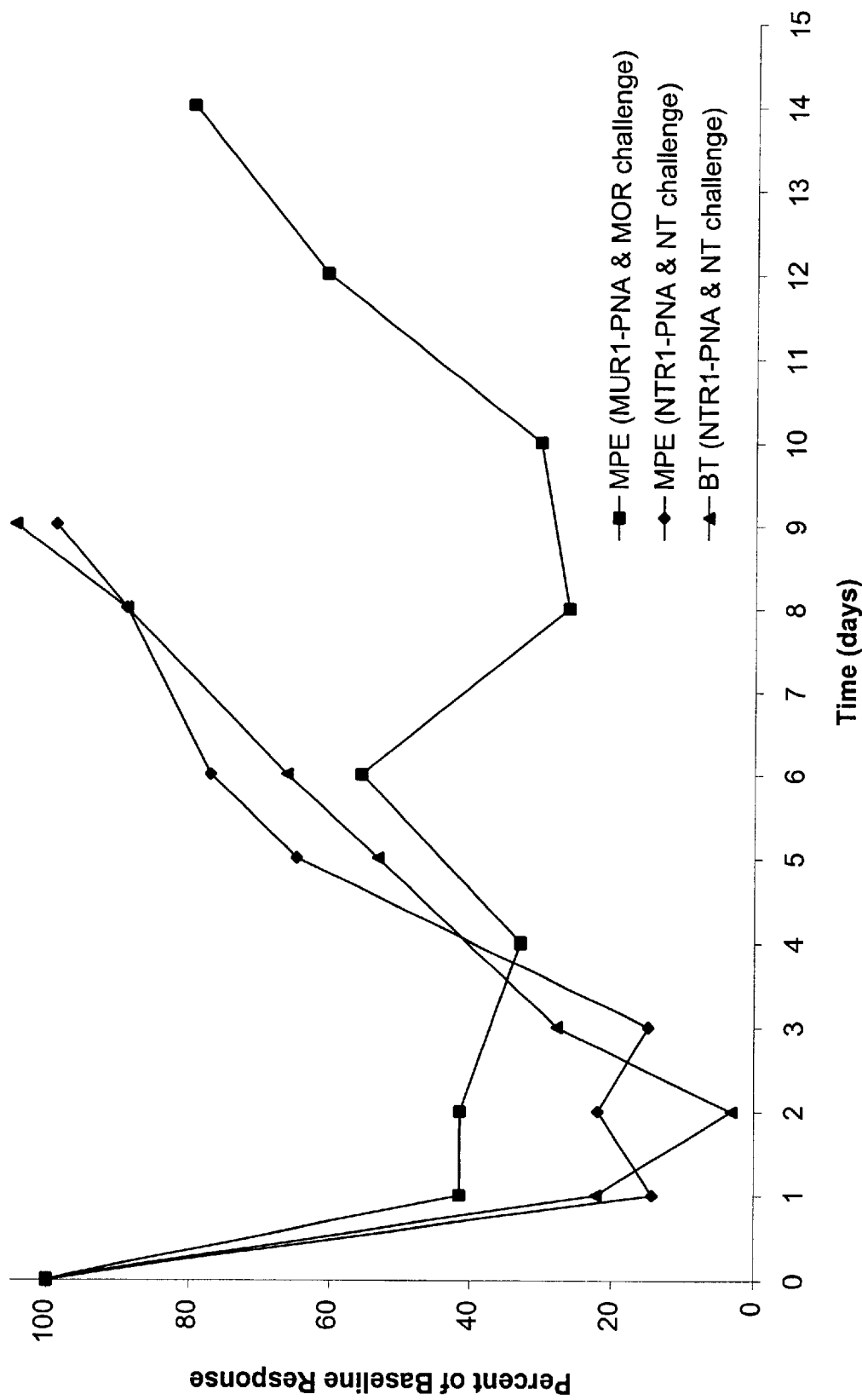
FIG. 9 is a graph plotting the maximal possible effect and body temperature as a percent of baseline response for rats treated intracranially on days −4, −2, and 0 with the indicated PNA oligomers and challenged with either NT or MOR.

To determine the relative turn-over rate of functional NTR1 and mu-1 receptors, a comparison was made between the biological responses influenced in rats by the administration of NTR1-PNA and MU1R-PNA oligomers. The MPE (hot plate) and BT responses for rats treated with NTR1-PNA oligomers and challenged with NT were compared to the MPE (tail flick) response for rats treated with MU1R-PNA oligomers and challenged with MOR (FIG. 9). Each rat received three injections into the PAG of either NTR1-PNA or MU1R-PNA oligomers on days −4, −2, and 0. The 100 percent values on day zero were derived from untreated control rats, whereas the NTR1-PNA and MU1R-PNA treated rats were first analyzed one day after the last injection on day 0. Since the time needed for MOR responsiveness to return to normal is greater than the time needed for NT responsiveness to return to normal, mu-1 receptors appear to have a slower relative turn-over rate.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating living cells, said method comprising extracellularly administering to said cells a polyamide nucleic acid oligomer containing neutral amide backbone linkages which is complementary to a target nucleic acid, under conditions wherein a biological response associated with said target in a sequence specific manner, said administration being in vivo.

2. The method of claim 1, wherein said method comprises detecting said biological response.

3. The method of claim 1, wherein said oligomer is carrier-free.

4. The method of claim 1, wherein said administration is an extracranial administration.

5. The method of claim 1, wherein said cells are within a mammal.

6. The method of claim 1, wherein said oligomer crosses a blood-brain barrier of a living organism.

7. The method of claim 1, wherein said oligomer has sequence specificity for a nucleic acid sequence that regulates the expression of or encodes a polypeptide, said polypeptide being expressed intracranially in a living organism.

8. The method of claim 1, wherein said oligomer has sequence specificity for a nucleic acid sequence that regulates the expression of or encodes a polypeptide, said polypeptide being expressed extracranially in a living organism.

9. The method of claim 8, wherein said polypeptide is expressed in the gastrointestinal tract.

10. The method of claim 7, wherein said polypeptide participates in cell signaling.

11. The method of claim 10, wherein said polypeptide participates in opioid signaling.

12. The method of claim 11, wherein said polypeptide is an opioid receptor.

13. The method of claim 12, wherein said receptor is a morphine receptor.

14. The method of claim 12, wherein said receptor is a neurotensin receptor.

15. The method of claim 12, wherein said oligomer comprises a sequence selected from the group consisting of SEQ ID NO:s 1 and 2.

16. The method of claim 1, wherein said biological response is a modification of polypeptide expression.

17. The method of claim 16, wherein said modification is a reduction in polypeptide expression.

18. The method of claim 1, wherein said biological response is characterized by a physiological change in a living organism.

19. A method of treating a mammal, said method comprising:
   a) extracellularly administering to said mammal a polyamide nucleic acid oligomer containing neutral amide backbone linkages, which is complementary to a target nucleic acid, under conditions wherein said oligomer engenders a biological response associated with said target in a sequence specific manner, and
   b) detecting said biological response.

20. The method of claim 19, wherein said oligomer is carrier-free.

21. The method of claim 19, wherein said administration is an extracranial administration.

22. The method of claim 21, wherein said oligomer crosses a blood-brain barrier of said mammal.

23. The method of claim 19, wherein said oligomer has sequence specificity for a nucleic acid sequence that regulates the expression of or encodes a polypeptide, said polypeptide being expressed intracranially in said mammal.

24. The method of claim 23, wherein said polypeptide participates in cell signaling.

25. The method of claim 24, wherein said polypeptide participates in opioid signaling.

26. The method of claim 25, wherein said polypeptide is an opioid receptor.

27. The method of claim 26, wherein said receptor is a morphine receptor.

28. The method of claim 26, wherein said receptor is a neurotensin receptor.

29. The method of claim 19, wherein said oligomer has sequence specificity for a nucleic acid sequence that regulates the expression of or encodes a polypeptide, said polypeptide being expressed extracranially in said mammal.

30. The method of claim 29, wherein said polypeptide is expressed in the gastrointestinal tract.

31. The method of claim 19, wherein said oligomer comprises a sequence selected from the group consisting of SEQ ID NO:s 1 and 2.

32. The method of claim 19, wherein said biological response is a modification of polypeptide expression.

33. The method of claim 32, wherein said modification is a reduction in polypeptide expression.

34. The method of claim 19, wherein said biological response is characterized by a physiological change in said mammal.

35. The method of claim 1, wherein said oligomer is acridine-free.

36. The method of claim 1, wherein said oligomer is protein-free.

37. The method of claim 1, wherein said oligomer is DNA-free.

38. The method of claim 1, wherein said oligomer is peptide-free.

39. The method of claim 1, wherein said oligomer is bis-PNA-free.

40. The method of claim 1, wherein said oligomer is biotin-free.

41. The method of claim 1, wherein said oligomer is fluorescein-free.

42. The method of claim 5, wherein the site of said administration is outside the central nervous system of said mammal.

43. The method of claim 42, wherein said administration is an intraperitoneal administration.

44. The method of claim 19, wherein said oligomer is acridine-free.

45. The method of claim 19, wherein said oligomer is protein-free.

46. The method of claim 19, wherein said oligomer is DNA-free.

47. The method of claim 19, wherein said oligomer is peptide-free.

48. The method of claim 19, wherein said oligomer is bis-PNA-free.

49. The method of claim 19, wherein said oligomer is biotin-free.

50. The method of claim 19, wherein said oligomer is fluorescein-free.

51. The method of claim 19, wherein the site of said administration is outside the central nervous system of said mammal.

52. The method of claim 51, wherein said administration is an intraperitoneal administration.

* * * * *

UNITED STATES PATENT AND TRADEMARK OFFICE
CERTIFICATE OF CORRECTION

PATENT NO.     : 6,472,209 B1
DATED           : October 29, 2002
INVENTOR(S)  : Elliott Richelson et al.

It is certified that error appears in the above-identified patent and that said Letters Patent is hereby corrected as shown below:

<u>Column 16,</u>
Line 39, after "wherein" please insert -- said oligomer engenders --.

Signed and Sealed this

Third Day of June, 2003

JAMES E. ROGAN
*Director of the United States Patent and Trademark Office*